(12) United States Patent
Mayelle et al.

(10) Patent No.: US 10,598,573 B2
(45) Date of Patent: Mar. 24, 2020

(54) METHOD FOR PRODUCING A CARBONATE BONDED, PRESS-MOULDED ARTICLE

(71) Applicant: RECOVAL BELGIUM, Farciennes (BE)

(72) Inventors: Nick Mayelle, Farciennes (BE); Frédérique Bouillot, Farciennes (BE); Dirk Van Mechelen, Farciennes (BE)

(73) Assignee: ORBIX SOLUTIONS, Farciennes (BE)

( * ) Notice: Subject to any disclaimer, the term of this patent is extended or adjusted under 35 U.S.C. 154(b) by 333 days.

(21) Appl. No.: 15/505,594

(22) PCT Filed: Aug. 28, 2015

(86) PCT No.: PCT/EP2015/069797
§ 371 (c)(1),
(2) Date: Feb. 21, 2017

(87) PCT Pub. No.: WO2016/030531
PCT Pub. Date: Mar. 3, 2016

(65) Prior Publication Data
US 2017/0241871 A1    Aug. 24, 2017

(30) Foreign Application Priority Data

Aug. 29, 2014    (EP) .................................... 14182955

(51) Int. Cl.
*B29B 13/00*    (2006.01)
*G01N 1/28*    (2006.01)
(Continued)

(52) U.S. Cl.
CPC ............. *G01N 1/286* (2013.01); *B30B 9/047* (2013.01); *B30B 9/06* (2013.01); *B30B 11/027* (2013.01);
(Continued)

(58) Field of Classification Search
CPC ......... G01N 1/286; B30B 11/027; B30B 9/06; B30B 9/047; C04B 28/087; C04B 28/082;
(Continued)

(56) References Cited

U.S. PATENT DOCUMENTS 5,650,562 A    7/1997    Jones, Jr.
6,264,736 B1    7/2001    Knopf et al.
(Continued)

FOREIGN PATENT DOCUMENTS

WO    2009/133120    11/2009
WO    WO-2013060870 A1 *    5/2013    ............. C04B 28/10

OTHER PUBLICATIONS

Ray et al., "Evaluation of Dust Generated from Basic Oxygen Furnace Steel Making", Journal of the Air & Waste Management Association, 47:6, 716-721 (1997) (Year: 1997).*
(Continued)

*Primary Examiner* — Galen H Hauth
(74) *Attorney, Agent, or Firm* — Ferguson Case Orr Paterson (57) ABSTRACT

The carbonate bonded, press-moulded article is produced by press-moulding a particulate, carbonatable material that contains water and by carbonating the obtained compact with carbon dioxide gas. In order to be able to ensure an optimal compressive strength of the article two types of tests are provided. In the first type of test a sample of the particulate material is compressed with an increasing compaction pressure and when water starts to be expelled from the material as from a particular compaction pressure, the press-moulding step is performed with a compaction pressure which is at least 7 MPa smaller than this compaction pressure. In the second type of test different samples of the particulate material are press-moulded with different compaction pressures and, after having released the compaction
(Continued)

pressure, the density of the compact is determined. In case this density decreases instead of increases as from a particular compaction pressure, the press-moulding step is performed with a compaction pressure which is smaller than this particular compaction pressure.

17 Claims, 6 Drawing Sheets (51) Int. Cl.
*B30B 9/04* (2006.01)
*B30B 9/06* (2006.01)
*B30B 11/02* (2006.01)
*C04B 28/08* (2006.01)
*C04B 28/02* (2006.01)

(52) U.S. Cl.
CPC ............ *C04B 28/021* (2013.01); *C04B 28/08* (2013.01); *C04B 28/082* (2013.01); *C04B 28/087* (2013.01); *Y02P 40/18* (2015.11); *Y02W 30/92* (2015.05); *Y02W 30/94* (2015.05)

(58) Field of Classification Search
CPC ...... C04B 28/08; C04B 28/021; Y02W 30/92; Y02W 30/94; Y02P 40/18
See application file for complete search history.

(56) References Cited

U.S. PATENT DOCUMENTS

2011/0248419 A1* 10/2011 Filali .................. B28B 7/44
264/82
2017/0073270 A1* 3/2017 Shao .................. E04C 1/00

OTHER PUBLICATIONS

International Search Report, International application No. PCT/EP2015/069797, dated Oct. 21, 2015.

* cited by examiner

METHOD FOR PRODUCING A CARBONATE BONDED, PRESS-MOULDED ARTICLE

The present invention relates to a method for producing a carbonate bonded, press-moulded article, which method comprises the steps of providing a particulate, carbonatable material that contains water; press-moulding the particulate material to form a compact; and carbonating the particulate material in said compact to produce carbonates thus transforming the compact into a carbonate bonded, press-moulded article. The carbonation step is carried out by bringing the compact in contact with a gas that contains at least 1 vol. % of carbon dioxide.

There are different industrial production processes which produce carbonatable materials as by-products. These by-products are for example fly ashes, bottom ashes (in particular municipal waste incineration bottom ashes) and slags generated during the production of phosphorus or during the production of ferrous or non-ferrous metals, such as zinc, copper and lead and iron or steel. Also dust from air filters for example from steel furnaces is carbonatable in particular when it contain calcium oxides. Some of these by-products can be used in different applications. Blast furnace slags can be used for example in road construction and also in the production of cement. Some slags, such as common steel slags (for example LD slags) which have a high neutralizing value can for example also be used as a soil conditioning agent. Other materials, such as bottom ashes and stainless steel slags contain however considerable amounts of heavy metals which are problematic in view of their leaching behaviour.

In order to limit the impact, both economic and environmental, of these domestic and industrial waste materials, attempts have been made more and more to develop methods of processing these materials, i.e. methods for converting these waste materials into economically valuable materials. A large quantity of these waste materials is alkaline and comprises carbonatable substances, such as calcium oxides and/or hydroxides and magnesium oxides and/or hydroxides. Other substances, for example calcium silicates contained in the waste materials, may also be carbonatable. It is known that the carbonation of these substances, makes it possible to obtain materials having good mechanical qualities. Moreover, carbonation may also help in preventing leaching of pollutants such as heavy metals.

It has for example been proposed, in WO-A-2007/096671, to proceed with an accelerated carbonation of waste in a rotary drum in order to produce a secondary granulate that can serve as a construction material. A similar process has been proposed for waste from the extraction or processing of metals in WO-A-2009/024826. In the materials obtained by these processes, the carbonation of lime, present in the waste, forms a calcareous matrix ensuring both less leaching of the heavy metals contained in the waste, and greater mechanical strength.

Stainless steel slags are a particular group of slags which contain relatively large amounts of chromium and often also of nickel and/or of molybdenum. As disclosed in EP-B-0837043, EP-B-1055647 and in EP-B-1146022 the leaching problems of stainless steel slags can be solved by crushing the steel slags, removing the valuable stainless steel particles therefrom and by applying the different fractions of the remaining crushed slags in bounded applications, for example as fine or coarse aggregate in concrete or asphalt. However, due to its higher gamma dicalcium silicate ($\gamma$-C2S) content, the finer fraction of these crushed steel slags (0-0.5 mm) has high water absorption properties and is thus not suited for being used in concrete or asphalt applications.

In order to be able to recycle more of the valuable stainless steel that remains in stainless steel slags, there is moreover an increasing interest in milling the crushed steel slags more finely so that more stainless steel can be recycled. The finely milled fraction, having for example a particle size of less than 100 µm, has a smaller gamma dicalcium silicate content than the above described fines since it is produced starting from a coarser fraction of the crushed steel slags (preferably a coarser fraction which has a relatively high content of steel, which can for example be obtained by a magnetic separation process). As disclosed for example in EP 2160367, this finely milled fraction can be used as filler in concrete or asphalt but other large-scale applications of this finely milled fraction would be very useful to be able to have a larger and even more valuable potential market for these fine waste materials.

To reduce the high water absorption of the fines removed from coarser fractions of crushed stainless steel slag so that not only these coarser fractions but also the fines can be used in concrete or asphalt, WO 2009/090219 proposes to aggregate and subsequently carbonate these fines under a relatively low pressure. In this way, aggregates having lower water absorption properties and the necessary strength for being used in concrete or asphalt could be produced. Another possible application of such aggregated and carbonated fines is disclosed in WO 2009/090226. In this application the aggregated and carbonated fines are introduced as a foaming slag former in an electric steel furnace.

Another carbonation method for producing more valuable construction materials starting from particulate carbonatable materials, in particular from the fines of crushed stainless steel slags which have a size of between 0 and 0.5 mm, is disclosed in WO-A-2009/133120. In this method the particulate material is first press-moulded with a relatively high compaction pressure of between 5 and 65 MPa, and the obtained compact is subsequently carbonated under a relatively high temperature and pressure. In this way, carbonated compacts with a relatively high compressive strength can be produced. By controlling the porosity and the intrinsic permeability of the compacts, and by carbonating for several hours (more particularly for 18 hours at an increased pressure and temperature), compressive strengths of between 26 and 66 MPa were obtained with a 0-500 µm fine stainless steel slag fraction which was press-moulded with a compaction pressure of 182 kg/cm$^2$ (=17.8 MPa). A drawback of this prior art method is that, notwithstanding the fact that relatively small blocks were carbonated (62×62×32 mm and 120×55×46 mm), high gas pressures were required which makes the process quite costly.

A problem of the prior art carbonation methods is moreover that, as described for example on p. 201 of the review article "A review of accelerated carbonation technology in the treatment of cement-based materials and sequestration of $CO_2$" of M. Fernández Bertos et al. in *Journal of Hazardous Materials* B112 (2004) 193-205, the water content of the particulate material should be high enough for the carbonation reaction but should be quite low to allow diffusion of the $CO_2$ into the compact. This is especially important when carbonating at low gas pressures, i.e. at pressures below 5 bars, and when compacting the particulate material with relatively large compaction pressures so that it has a reduced porosity. In case the water content of the particulate material is too high, it therefore has to be dried. This is for example the case for the stainless steel slag fines which are separated off from the coarser fractions of crushed stainless steel slags. Compared to these coarser fractions, the fines have a relatively high gamma dicalcium silicate content (so-called falling steel slag produced by the expansive transformation of beta dicalcium silicate to gamma dicalcium silicate upon cooling the stainless steel slag) and absorb more water. They have in particular a particle size of between 0 and 0.5 mm and are separated off in practice from the coarser sand fraction (having a particle size larger than 0.5 mm) of the stainless steel slags by a wet separation technique. Even when allowing these wet fines to dry for a long time under atmospheric conditions, they still have a moisture content of about 17% by dry weight which hampers the carbonation process. Although penetration of the carbon dioxide into the compact was enhanced by the high pressure in the high pressure carbonation process disclosed in WO 2009/133120 the fines were still first dried to a moisture content of 12% by weight. A drawback of such a drying process is however that it requires a lot of time and energy since the water is strongly absorbed, i.a. by capillary forces, within the stainless steel slag particles.

When press-moulding the particulate material to form the compact which is to be carbonated, the green strength of the compact should preferably be sufficiently high so that it can be handled more easily without falling apart or being damaged. For a relatively low compaction pressure, corresponding to a same compaction degree as obtained in the Proctor test (described in ASTM D698/AASHTO T99), the maximum green strength, or a minimum porosity, is obtained for a water content corresponding to the Proctor density. As described in WO 2009/090219 the 0-0.5 mm fines of stainless steel slags have for example an optimal Proctor density for a water content of 22 wt. %. At this optimal water content, the smallest compaction pressures are required to obtain a certain green strength. At lower water contents, higher compaction pressures are generally needed to obtain a same reduction of the porosity and thus a same increase of the compressive strength. In practice, it is thus advantageous to apply higher water contents in the particulate material in order to be able to achieve higher green strengths, but, on the other hand, lower water contents are required to enable to obtain an optimal carbonation degree.

An object of the present invention is now to provide a new method for producing carbonate bonded, press-moulded articles which enables to ensure obtaining optimal compressive strengths of the press-moulded and carbonated compacts both for lower water contents, which enable to achieve the required green strength (compressive strength) with a relatively high compaction pressure, and for higher water contents, which enable to achieve the required green strength with a relatively small compaction pressure and which have the advantage that no or less drying of the particular material is needed in case of relatively wet particulate materials.

To this end the method of the present invention is characterised in a first aspect in that, before press-moulding the particulate material to form said compact, a series of tests is performed wherein for each compaction pressure of a series of increasing compaction pressures, ranging from a lowermost to an uppermost compaction pressure, at least one sample of the particulate material is press-moulded with said compaction pressure and, after having released the compaction pressure, a parameter indicative of the density of the press-moulded sample is determined. The particulate material is subsequently press-moulded to form said compact with a compaction pressure which is selected within a range delimited by a lower and an upper compaction pressure limit. The lower compaction pressure limit is higher than 5 MPa whilst the upper compaction pressure limit is equal to or smaller than said uppermost compaction pressure and, in case the density decreases when in said series of tests the compaction pressure is increased from a smaller compaction pressure of said series of compaction pressures to a larger compaction pressure of said series, said upper compaction pressure limit is smaller than said larger compaction pressure and preferably equal to or smaller than said smaller compaction pressure.

According to this first aspect of the invention it has been found that a too high compaction pressure may have a negative effect on the compressive strength of the carbonated compact. It has in particular been found that such a negative effect occurs when applying a compaction pressure which is so high that the density of the compact, measured after having released the compaction pressure, decreases instead of increases notwithstanding the fact that the particulate material was initially compressed to a higher density in the press mould. Starting from a certain compaction pressure the compressed particulate material was thus found to expand back to a larger volume upon release of the compaction pressure. Although this expansion occurred prior to the carbonation step, the compressive strength of the carbonated compact was found to be negatively affected by this expansion. The observed negative effect was found to be so large that the compressive strength of the carbonated compact compressed with a too high compaction pressure was even considerably lower than the compressive strength of a carbonated compact compressed to a same density in the mould with a considerably lower compaction pressure. The method according to the first aspect of the invention enables to avoid this negative effect on the compressive strength of the carbonated compact so that, in order to maximize this compressive strength, the compaction pressure may be increased up to the upper compaction pressure limit as determined in accordance with the method of the first aspect of the present invention.

According to the invention it has also been found that, in case the particulate material has a relatively high water content, the water contained in the particulate material may also have a considerable negative effect on the compressive strength of the carbonated compact. In order to enable to minimize this negative effect, the method of the invention is characterised in a second aspect in that, before press-moulding the particulate material to form said compact, at least one sample thereof is subjected to a test wherein the sample is compressed with an increasing compaction pressure until a predetermined compaction pressure is reached or, in case the particulate material has such a high water content that, when compressing the sample, water starts to be expelled from said sample as from a lower compaction pressure, which is lower than said predetermined compaction pressure, at least until said lower compaction pressure is reached. The particulate material is then press-moulded to form said compact with a compaction pressure which is selected within a range delimited by a lower and an upper compaction pressure limit. In the method of the second aspect of the present invention, the lower compaction pressure limit is again higher than 5 MPa whilst the upper compaction pressure limit is at least 7 MPa smaller than said predetermined compaction pressure and at least 7 MPa smaller than said lower compaction pressure in case the particulate material has said high water content.

According to this second aspect of the invention it has been found that when the particulate material comprises such an amount of water that when press-moulding the particulate material water is expelled therefrom, the carbonated compact has a strongly reduced compressive strength. However, notwithstanding the quite high water content, a considerably higher compressive strength can according to the second aspect of the invention be obtained by using a lower compaction pressure, more particularly a compaction pressure which is at least 7 MPa lower than the compaction pressure as from which water starts to be expelled from the particulate material.

When applying the second aspect of the invention in combination with the first aspect, in case of a relatively high water content, the upper compaction pressure limit should thus be at least 7 MPa smaller than the compaction pressure as from which water starts to be expelled from the particulate material even when the upper compaction pressure limit determined in accordance with the first aspect of the invention would be higher. In case of relatively dry particulate materials, the upper compaction limit should be lower than the compaction pressure as from which the density of the decompressed compact would decrease instead of increase and the compaction pressure as from which water would start to be expelled from the particulate material does not need to be determined (as no water is expelled or only at compaction pressures which are at least more than 7 MPa higher than the uppermost compaction pressure applied in the tests of the first aspect of the invention).

In an advantageous embodiment of the method according to the present invention said upper compaction pressure limit is smaller than 60 MPa, preferably smaller than 50 MPa and more preferably smaller than 40 MPa and/or said lower compaction pressure limit is larger than 7 MPa, preferably larger than 10 MPa and more preferably larger than 15 MPa.

It has been found that for such compaction pressures, maximum compressive strengths can be achieved. The tests provided in the first and the second aspects of the present invention enable to avoid compaction strengths which would result in bad compressive strengths of the carbonated articles. This is the case when the particulate material has a relatively high water content which may negatively affect the compressive strength of the carbonated compact if too high compaction pressures are applied and/or when the particulate material has such properties that when compacting it too strongly, the density of the compact increases instead of decreases.

In a preferred embodiment of the method according to the present invention the particulate material comprises slag from a metal production process, slag from the production of phosphorus, bottom ash and/or fly ash, the particulate material preferably comprises steel slag, in particular stainless steel slag.

In a further preferred embodiment of the method according to the present invention at least 50 vol. % of said particulate material has a particle size smaller than 1000 μm, preferably smaller than 500 μm, more preferably smaller than 250 μm and most preferably smaller than 100 μm and at least 50 vol. % of said particulate material has a particle size larger than 1 μm, preferably larger than 5 μm and more preferably larger than 10 μm.

In a still further preferred embodiment of the method according to the present invention the particulate material which is press-moulded to form said compact has a water content of at least 1%, preferably at least 3% and more preferably at least 5% by dry weight.

A minimum amount of water is required for the carbonation step, in particular at least 1% by dry weight, whilst higher water contents are advantageous to achieve higher green strengths of the compact.

In an advantageous embodiment of the method according to the present invention the gas used to carbonate the compact is at a gauge pressure of less than 0.5 MPa, preferably at a gauge pressure of less than 0.2 MPa and more preferably at a gauge pressure of less than 0.1 MPa. By gauge pressure is meant the pressure above the ambient pressure. The absolute pressure is preferably at least equal to the atmospheric pressure or at most somewhat below atmospheric pressure, in particular at most 0.02 MPa, preferably at most 0.01 MPa below atmospheric pressure.

An advantage of such low pressure carbonation process is that it is easier and less expensive to carry out and also requires less expensive equipment than the so-called high pressure carbonation processes. By selecting the claimed compaction pressures, high compressive strengths can moreover be achieved with such low pressures. Moreover, tests have shown that lower gas pressures enable to achieve higher compressive strengths when a same amount of carbonates is produced.

Other particularities and advantages of the invention will become apparent from the following more detailed description of some particular embodiments. The reference numerals used in this description relate to the annexed drawings wherein.

The present invention generally relates to a method for producing a carbonate bonded, press-moulded article by press-moulding and carbonating a particulate, carbonatable material.

The expression "particulate material", or also "granular material", refers to any material which consists of loose particles. These particles may be of different sizes so that the expression "particulate material" not only embraces coarse or fine granulates but also very fine granulates, in particular powders. The particulate material applied in the method according to the present invention has however preferably such a particle size, or particle size distribution, that at least 50 vol. % of the particulate material has a particle size smaller than 1000 μm, preferably smaller than 500 μm, more preferably smaller than 250 μm and most preferably smaller than 100 μm. On the other hand, at least 50 vol. % of the particulate material has preferably a particle size larger than 1 μm, more preferably larger than 5 μm and most preferably larger than 10 μm.

The particulate material may consist of one particulate material which is carbonatable or it may consist of a mixture of at least one first particulate material, which is carbonatable, and at least one second particulate material which may be carbonatable or not. A particulate material which is not carbonatable comprises for example dust extracted from flue gasses from a steel converter, waste resulting from deburring of steel parts or mixtures thereof. Such a particulate material may comprise in particular more than 30%, preferably more than 40% and more preferably more than 50% by dry weight of metallic iron and more than 1%, preferably more than 4% and more preferably more than 8% by dry weight of iron oxides. The carbonate bonded, press-moulded article which comprises such a second particulate material bonded together by means of a carbonatable first particulate material is preferably fed to a blast furnace so that the metals contained therein are recycled. It can also be fed to a steel furnace, in particular to a steel converter, but feeding it to a blast furnace has the advantage that the carbonated material has not to be dried after the carbonation step.

The granulometry of the particulate material, or of the mixture of the first and second particulate materials, is preferably selected to achieve a higher packing density, or in other words a smaller total porosity, since in this way a higher compressive strength can be obtained. The compressive strength of the compact before the carbonation step, i.e. the green strength of the compact, as well as the compressive strength of the carbonated compact is determined in accordance with the European standard EN 12390-3:2009.

The particulate material which is carbonatable, i.e. the carbonatable material as a whole or, in case of the above described mixtures of first and second particular material, the first particulate material and/or the second particulate material when it is carbonatable, comprises preferably a by-product or a waste product. The particulate material which is carbonatable has in particular a pH of at least 8.3 and comprises a source of at least one alkaline earth metal, in particular calcium. The pH of the carbonatable material is defined as the pH of demineralised water wherein the particulate material has been immersed for 18 hours in a liquid/solid ratio of 4.5. The carbonatable material may contain different crystalline and amorphous phases and preferably contains at least one alkaline earth metal silicate phase, in particular crystalline dicalcium silicate.

The particulate material which is carbonatable also preferably comprises calcium oxide and/or calcium hydroxide, the total amount of calcium oxide and calcium hydroxide being preferably at least 1% by dry weight, more preferably at least 2% by dry weight. It may also contain magnesium oxide and/or magnesium hydroxide. These oxides and hydroxides may be in an amorphous and/or in a crystalline form, in particular in the form of portlandite ($Ca(OH)_2$), free lime (CaO), brucite ($Mg(OH)_2$) and in the form of periclase (MgO). Initially, as they are often produced under high temperatures, the freshly produced carbonatable materials usually contain no hydroxides but only oxides, the hydroxides being formed upon aging (weathering) of the carbonatable material or during the carbonation step. As the air also contains a small amount of carbon dioxide, upon aging of the carbonatable material a portion of the hydroxides is further transformed into carbonates (by natural carbonation).

A wide variety of carbonatable materials is suitable for being processed in accordance with the method according to the present invention. Suitable carbonatable materials are for example bottom ashes, more particularly bottom ashes produced during the incineration of waste, in particular of municipal waste (i.e. municipal waste incineration bottom ashes). Also fly ashes can be carbonated, in particular non-coal fly ashes and moreover filter dust from a steel furnace, in particular from an electric arc furnace (EAF filter dust). Most preferred carbonatable materials are however slag materials resulting from metal production processes (production of pig iron, steel, stainless steel and production of non-ferrous metals such as copper and zinc) and from the production of phosphorus. The used carbonatable material is preferably a non-hydraulic, or substantially non-hydraulic material. Since a non-hydraulic material cannot provide as such a settable matrix by reaction with water (in particular by CSH formation), a solid article can still be produced by carbonation of this material.

The slag material may be a blast furnace slag but it is preferably a steel making slag, more preferably a stainless steel making slag. Steel making slags may be converter slags (such as LD slags) or electric arc furnace slags (EAF slags). Common steel making slags do not contain or only small amounts of heavy metals such as chromium and nickel and therefore do not present leaching problems as stainless steel slags do. Stainless steel slags generally contain more than 3000 mg/kg chromium and usually even more than 5000 mg/kg chromium. They may also contain nickel, more particularly more than 300 mg/kg, in particular more than 400 mg/kg and often even more than 500 mg/kg nickel. By carbonating these carbonatable slags, leaching of these heavy metals can be reduced or even prevented.

Figure 1:
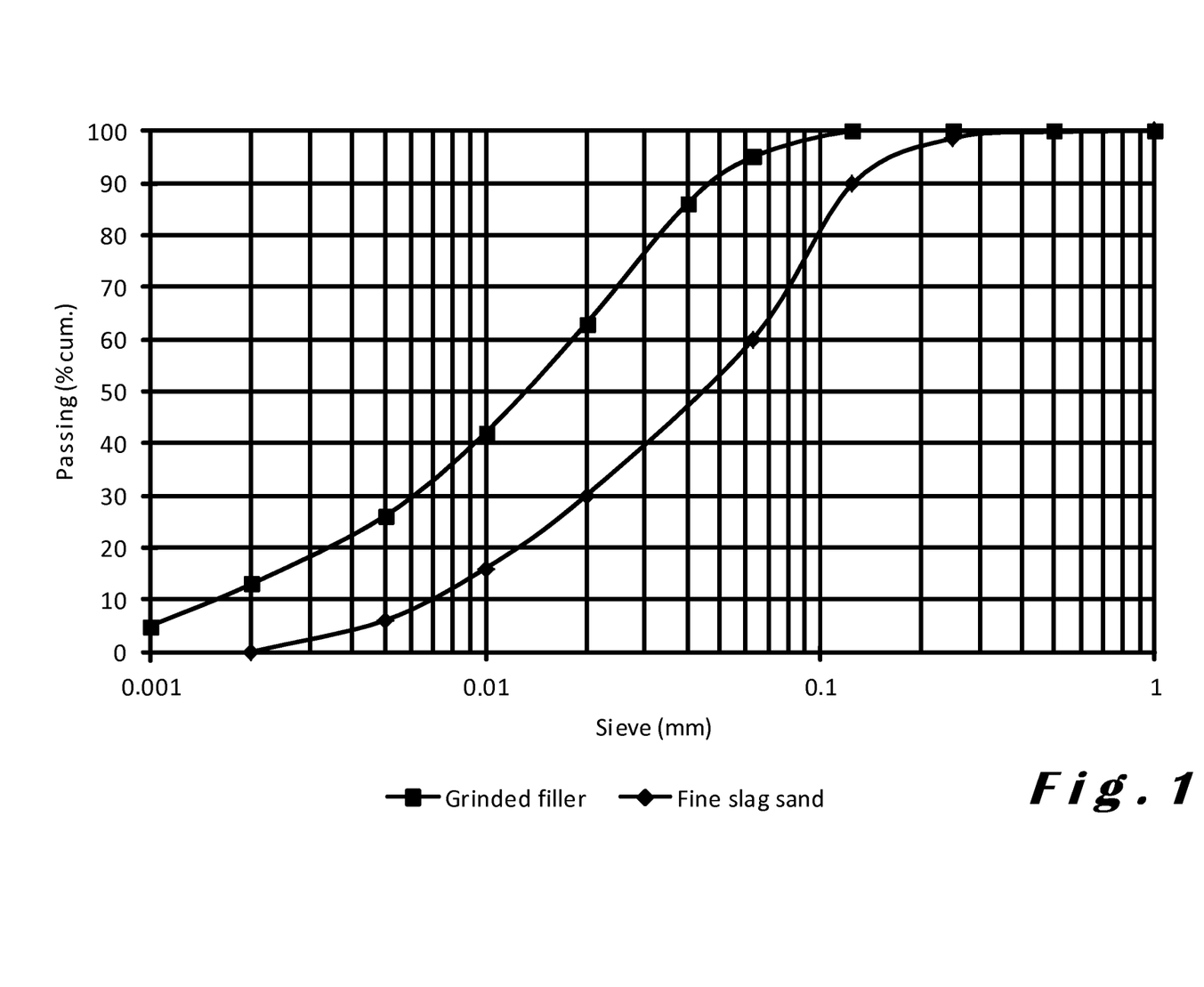
FIG. 1 shows the particle size distribution (cumulative passing in vol. % versus the particle size) of the stainless steel slag filler fraction used in Experiment 1 and of the fine stainless steel slag sand fraction used in Experiment 2.

Steel slags, and in particular stainless steel slags, are usually crushed to produce a granular material from which the metal fraction can be recycled. The coarser fraction of the crushed stainless steel slag can be used as coarse or fine aggregate in concrete of asphalt. The finer fraction, in particular the 0-500 μm fraction, has however too high water absorption properties so that it is not suitable, as such, for these applications. The finer fraction, i.e. the so-called fines, contains indeed a larger amount of gamma dicalcium silicate ($\gamma$-C2S) which is produced during the solidification of the liquid slag when a portion of the beta dicalcium silicates ($\beta$-C2S) is further transformed in the gamma polymorph. Due to the resulting expansion, cracks are formed and a so-called falling slag is produced which has high water absorption properties. This stainless steel slag material, which contains in particular at least 3% by dry weight, more particularly at least 5% by dry weight and even more particularly at least 7% by dry weight of $\gamma$-C2S is preferably used as particulate material, or as one of the particulate materials, in the method of the present invention. FIG. 1 represents the particle size distribution, as cumulative values of the particles which pass through different sieves, of such a fine stainless steel slag fraction (% by volume versus the particle size/sieve size in mm).

As described in WO 2008/145758 it is also possible to grind a coarser fraction of the crushed stainless steel slag to a fine particle size, in particular to obtain a filler which can be used in asphalt or in concrete. Since the fines (which are rich in $\gamma$-C2S) were removed from this coarser fraction, it has a lower $\gamma$-C2S content, in particular a $\gamma$-C2S content which is lower than 7% by dry weight or even lower than 5% by dry weight. A finer milling or grinding of the coarser fraction enables to recycle more valuable metal. The coarser fraction which is finely milled is preferably separated off, for example by a magnetic separation technique, so as to have a higher metal content than the remaining slag fraction. FIG. 1 also represents the particle size distribution, as cumulative values of the particles which pass through different sieve sizes, of a sample of a finely grinded stainless steel slag fraction (% by volume versus the particle size/sieve size in mm).

In the method of the present invention, which is illustrated schematically in FIG. 2, the particulate, carbonatable material 1 is applied in a mould 2 and is compressed therein to form a compact 3. The mould 2 illustrated in FIGS. 2A to 2C is provided with a lid 4 onto which the required pressure can be exerted. This can be done by means of a hydraulic pressure mechanism which is known per se and only the piston rod 5 of which is shown in FIG. 2C. After having press-moulded the carbonatable material 1, with a compaction pressure which is in accordance with the present invention higher than 5 MPa, the produced compact is carbonated by means of a gas, which contains at least 1 vol. % of carbon dioxide, thereby producing carbonates which transform the compact 3 in the carbonate bonded, press-moulded article.

Figure 2A:
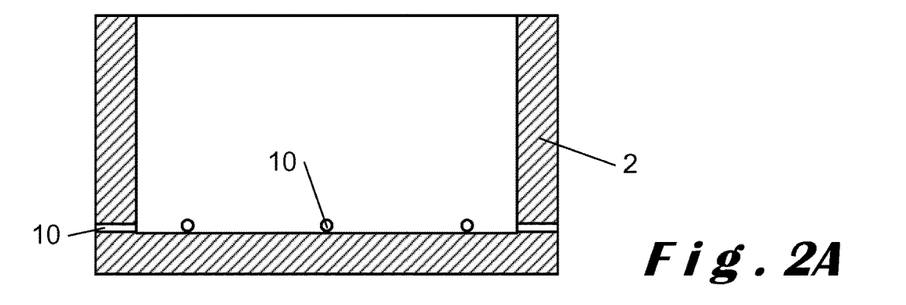
FIGS. 2A to 2D illustrate schematically the method carried out in Experiments 1 and 2 to produce the carbonated, press-moulded compacts.
Figure 2B:
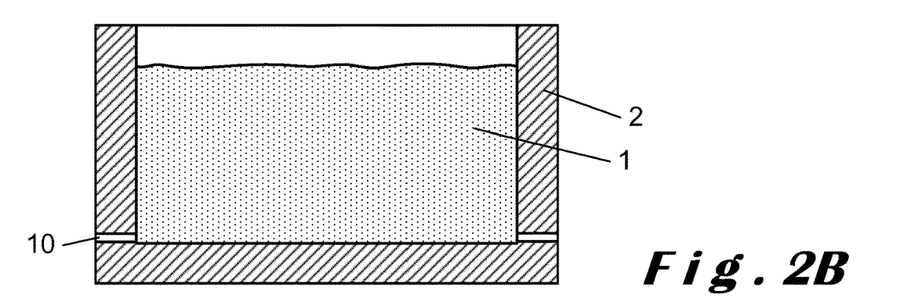
Figure 2C:
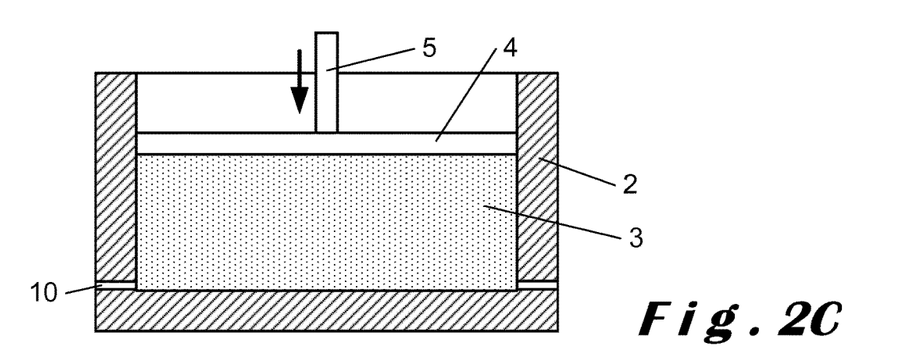
Figure 2D:
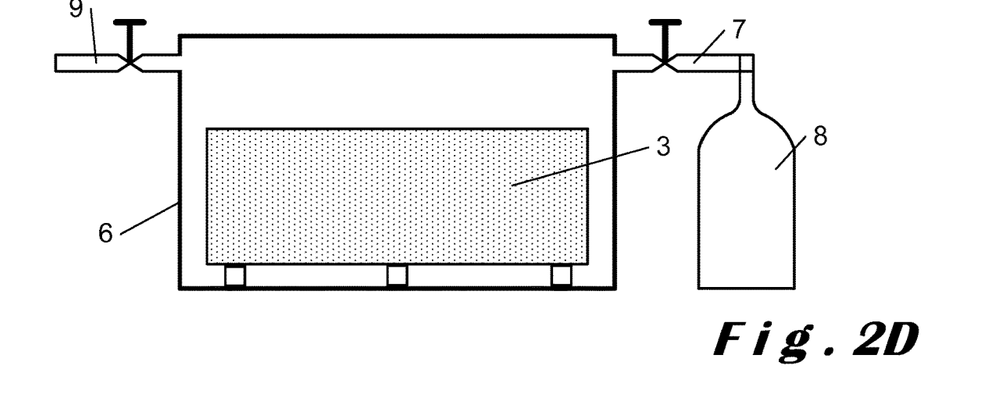

As illustrated in FIG. 2D, the compact 3 can be put into a closed container 6 wherein the carbon dioxide containing gas is introduced through an inlet 7. The carbon dioxide containing gas can be stored in a pressurized gas bottle 8, which may contain in particular substantially pure carbon dioxide gas. In an initial phase, the container 6 can be purged through the inlet 7 and the outlet 9 with pure carbon dioxide so that the carbonation is performed with nearly pure carbon dioxide gas. Less concentrated gasses can however also be used, for example exhaust gasses from industrial processes. The gas used for carbonating the compacts comprises preferably at least 3 vol. %, more preferably at least 5 vol. % and most preferably at least 7 vol. % of carbon dioxide. Higher carbon dioxide contents of at least 20, 50 or 75 vol. % are even more preferred especially in order to accelerate the carbonation process.

The gas pressure in the container 6 is preferably controlled to be less than 0.5 MPa, preferably less than 0.2 MPa and more preferably less than 0.1 MPa above atmospheric pressure, i.e. the gauge pressure is preferably less than these pressure values. When shutting of the gas bottle 8, the pressure within the container may drop somewhat below atmospheric pressure as a result of the consumption of carbon dioxide gas.

The method according to the present invention provides two types of tests intended be carried out before press-moulding the particulate material 1 and enabling to ensure in a quick and easy way that the produced carbonated articles will have the required compressive strength without knowing important properties of the particulate material such as the water content, the porosity after press-moulding and the effect of an increasing compaction pressure onto the porosity. By means of these two types of tests a range of compaction pressures can more particularly be determined wherein the compaction pressure used to produce the compacts can be selected. This range is delimited by an upper and a lower compaction pressure limit. Since the porosity of the compact decreases as the compaction pressure increases, higher compaction pressures, i.e. compaction pressures closer to the upper limit, can be selected within this range in case higher compressive strengths are needed.

In a first aspect of the invention, a series of tests is performed wherein for each compaction pressure of a series of increasing compaction pressures, ranging from a lowermost to an uppermost compaction pressure, at least one sample of the particulate material is press-moulded with the respective compaction pressure. After having released the compaction pressure, a parameter indicative of the density of the press-moulded sample is determined.

In case the samples are all of a same weight, this parameter can simply be the volume of the press-moulded sample or even more simply the height of the press-moulded sample. In case the samples do not have identical weights, the respective weight has to be divided by the measured volume to obtain the density. Alternatively, the weight can also be divided by the height of the press-moulded sample to obtain a parameter which is indicative of the density of the press-moulded sample.

The upper compaction pressure limit of the range wherein the compaction pressure used for press-moulding the particulate material is to be selected, is first of all at least equal to or smaller than the uppermost compaction pressure applied in the series of tests. In case a decrease instead of an increase of the density is observed when the compaction pressure is increased in said series of tests from a smaller compaction pressure to a larger compaction pressure, the upper compaction pressure limit should be smaller than this larger compaction pressure, and should preferably be equal to or smaller than the smaller compaction pressure. It has indeed been observed that when the density of the press-moulded particulate material, measured after having released the compaction pressure, decreases instead of increases, the compressive strength of the carbonated compacts decreases considerably. Consequently, the upper compaction pressure limit should be sufficiently low so that such a decrease of the density does not occur within the range wherein the compaction pressure is to be selected.

Depending on the type of particulate material, a decrease of the density does not occur or only at higher compaction pressures. The uppermost compaction pressure which is applied in the series of tests is selected based on the compaction pressures that are feasible in practice. Moreover, in case the density of the compacts does not decreases when the compaction pressure is increased, such high compaction pressures do not have to be applied since no additional strength is achieved therewith. On the contrary, too large compaction pressures may damage the particles. Since it has been found that good compressive strengths can already be obtained with relatively low compaction pressures, the upper compaction pressure limit is therefore preferably smaller than 60 MPa, more preferably smaller than 50 MPa and most preferably smaller than 40 MPa. The uppermost compaction pressure applied in the series of tests therefore doesn't have to be larger than these upper limits. As mentioned hereabove, the lower compaction pressure limit should be higher than 5 MPa. Preferably, this lower compaction pressure limit is higher than 7 MPa, more preferably higher than 10 MPa and most preferably higher than 15 MPa. In general, higher compressive strengths are obtained with higher compaction pressures due to the reduced porosity of the compact unless, as explained hereabove, the higher compaction pressure would result in a decrease instead of an increase of the density of the compact (measured after having removed the compaction pressure).

In case the particulate material has a relatively high water content, this water content determines, in a second aspect of the invention, the upper compaction pressure limit of the range wherein the compaction pressure should be selected. In this second aspect of the invention, at least one sample of the particulate material is subjected to a water saturation test wherein the sample is compressed with an increasing compaction pressure until a predetermined compaction pressure is reached or, in case the particulate material has such a high water content that, when compressing the sample, water starts to be expelled from said sample as from a lower compaction pressure, which is lower than said predetermined compaction pressure, at least until said lower compaction pressure is reached.

The upper compaction pressure limit of the range wherein the compaction pressure used for press-moulding the particulate material is selected, is first of all at least 7 MPa smaller than the predetermined compaction pressure applied in the water saturation test. In case the particulate material has such a high water content that water is already expelled from the particulate material when reaching a lower compaction pressure, the upper compaction pressure limit should be at least 7 MPa smaller than this lower compaction pressure. It has indeed been observed that when compressing the particulate material with such a compaction pressure that water starts to be expelled therefrom, or even with a compaction pressure which is somewhat lower, more particularly less than 7 MPa lower, the compressive strength of the carbonated compacts decreases considerably. On the other hand it has been found that even with relatively high water contents good compressive strengths can be obtained when applying lower compaction pressures, i.e. compaction pressures which are at least 7 MPa lower than the compaction pressure at which water starts to be expelled from the compressed particulate material.

Preferably, the upper compaction pressure limit of the range within which the compaction pressure to be applied to press-mould the particulate material is selected is at least 10 MPa smaller than the uppermost compaction pressure applied in the water saturation test and at least 10 MPa smaller than said lower compaction pressure as from which water starts to be expelled from the particulate material.

Depending on the water content of the particulate material, no water is expelled or only at higher compaction pressures. The predetermined compaction pressure which is applied in the water saturation test as uppermost compaction pressure is selected based on the compaction pressures that are feasible in practice. Since it has been found that good compressive strengths can already be obtained with relatively low compaction pressures, the upper compaction pressure limit is preferably smaller than 60 MPa, more preferably smaller than 50 MPa and most preferably smaller than 40 MPa. The uppermost compaction pressure applied in the water saturation test should therefore doesn't have to be larger than 7 MPa above these upper limits. As mentioned hereabove, the lower compaction pressure limit should be higher than 5 MPa. Preferably, this lower compaction pressure limit is higher than 7 MPa, more preferably higher than 10 MPa and most preferably higher than 15 MPa.

Preferably both the density test and the water saturation test are carried out. If both the density test and the water saturation test are carried out, both tests result in a range wherein the compaction pressure is to be selected. In case the range obtained by the density test is not the same as the range obtained by the water saturation test, the overlapping part of both ranges should be determined and the compaction pressure should be selected within this overlapping part of both ranges thereby meeting both the density test and the water saturation test.

The particulate material preferably contains at least a minimum amount of water, in particular an amount of at least 1% by dry weight, so that during the carbonation step no water has to be supplied, for example via the carbon dioxide containing gas, to enable the carbonation reaction. Higher water contents, in particular water contents of at least 3% by dry weight and preferably of at least 5% by dry weight are, however, preferred in particular in view of enabling to achieve compacts having a higher green strength. The water content of the particulate material can be increased by adding water thereto in order to increase the green strength of the compacts, in particular to a compressive strength which is larger than 1 MPa, preferably larger than 2 MPa and more preferably larger than 3 MPa. The water saturation test enables to increase the water content to such an extent that a maximum green strength is obtained whilst still obtaining the required compressive strength after the carbonation step. The water saturation test allows indeed to determine easily when the water content becomes too high so that the maximum compaction pressure that can be used to press-mould the particulate material becomes too low to achieve a sufficient compaction of the particulate material. This maximum compaction pressure should in particular remain larger than the lower compaction pressure limit of 5 MPa, preferably of 7 MPa, more preferably of 10 MPa and most preferably of 15 MPa.

In case the particulate material has such a high water content that the required compressive strength cannot be achieved, in particular in case the upper compaction pressure limit of the range determined by means of the water saturation test would be lower than the lower compaction pressure limit of that range (which is higher than 5 MPa, preferably higher than 7 MPa, more preferably higher than 10 MPa and most preferably higher than 15 MPa), the water content of the particulate material can be decreased before the press-moulding step, in particular by drying. The water content is in particular reduced to a predetermined water content which is higher than 3% by dry weight and preferably higher than 5% by dry weight.

In view of the costs of a drying step, such a drying step is preferably avoided. This can be done by composing the particulate material as a mixture of an amount of a first particulate material, having a first water content, with an amount of a second particulate material, having a second water content which is lower than the first water content, and by decreasing the ratio between the amount of the first particulate material to the amount of the second particulate material. In the same way, if the water content of the particulate material would be too high, the water content can be reduced again by composing the particulate material as a mixture of said first and second particulate materials but by increasing instead of decreasing the ratio between the amount of the first particulate material to the amount of the second particulate material.

The first particulate material, i.e. the material having the highest water content, can be in particular a stainless steel slag material which contains at least 3% by dry weight, in particular at least 5% by dry weight and more particularly at least 7% by dry weight of γ-dicalcium silicate. This first particulate material can thus be the so-called fines of a stainless steel slag. In practice they have a quite high water content of for example between 15 and 20% by dry weight and are difficult to dry since the water is strongly absorbed in the particulate material.

The second particulate material, i.e. the material having the lowest water content, can be in particular a stainless steel slag material which contains less γ-dicalcium silicate than the first particulate material. This second material can thus consist of a coarser stainless steel slag fraction that has been milled to a finer particle size, in particular so that at least 50 vol. % of the second particulate material has a particle size smaller than 1000 μm, preferably smaller than 500 μm, more preferably smaller than 250 μm and most preferably smaller than 100 μm. When dry milling the coarser stainless steel slag fraction, it has been found that the resulting fine material has a low water content, in particular a water content of less than 0.3% by dry weight.

The second material may also be a particulate material that is not carbonatable. It could for example comprise the waste, i.e. the fine steel particles, resulting from deburring of steel parts and also dust extracted from/filtered out of flue gasses from a steel converter in case these flue gasses comprise for example fine steel particles which are fed into the steel furnace but a considerably portion of which may be blown out of the furnace by the upward draft generated therein.

EXPERIMENTAL RESULTS

Experiment 1

Filler Fraction

A stainless steel slag material was crushed to a particle size of between 0 and 35 mm and was separated in a 10 to 35 mm fraction and a 0 to 10 mm fraction. The 0 to 10 mm fraction was separated in a 0 to 2 mm fraction and in a 2 to 10 mm fraction.

From the 0 to 2 mm fraction, the steel particles were removed and the fraction was separated in a coarse sand fraction of 0.5 to 2 mm and in a fine sand fraction of 0 to 0.5 mm.

By means of a wet jigging apparatus, steel particles were removed from the 2 to 10 mm fraction. The remaining slag fraction was magnetically separated in a fraction which was still relatively rich in metal and a fraction which contained less metal. The metal rich fraction was milled, by a dry milling process, to a size of less than 100 μm and the metal particles were removed therefrom. The particle size distribution of the remaining slag fraction, i.e. the so-called filler fraction, is shown in FIG. 1. This filler fraction had a water content of less than 0.3% by dry weight. A chemical analysis showed that the filler fraction contained no hydroxides or carbonates. When putting this filler fraction in an atmosphere which is saturated with water at a temperature of 20° C., it only absorbed about 1% by dry weight of water.

By means of a pycnometer the density of the filler particles was determined to be 3392 kg/m$^3$. The bulk density of the filler fraction, compacted by its own weight, was equal to 1053 kg/m$^3$ so that it had a porosity of 69%.

1500 g of this filler fraction was mixed with different amounts of water (expressed as percent by dry weight of the dry filler fraction). The mixtures were put in a mould of 14 cm×10 cm×8 cm and were press-moulded with different compaction pressures. As illustrated in FIG. 2A the side walls of the mould were provided underneath with holes 10 so that water could be expelled from the particulate material at higher water contents and compaction pressures. After the press-moulding step, the obtained compacts were transferred to a glass container of 2 litres for the carbonation step. The period between adding the water to the particulate material and the start of the carbonation step was less than 15 minutes.

During the carbonation step, the glass container was kept in a water bath having a temperature of 30° C. Initially, the container was purged for 1 minute with 100% pure, dry carbon dioxide gas. The outlet of the container was then closed and the carbon dioxide was maintained in the container at a gauge pressure of between 0.01 and 0.02 MPa. After 24 hours the carbonated compacts were dried for 2 hours at 105° C. and the compressive strength of the carbonated compacts was determined in accordance with the European standard EN 12390-3:2009. Each experiment was done with five repetitions and the average values of the different values are indicated in Table 1.

TABLE 1

Experiments with the carbonation of the stainless steel slag filler fraction press-moulded with different compaction pressures and having different water contents.

| Exp. | Comp. pressure (MPa) | Water (wt. %) | Total porosity (vol. %) | Unsat. porosity (vol. %) | Compr. strength (MPa) | $CO_2$ uptake (%) | Dry density (g/cm$^3$) | Water expelled |
|---|---|---|---|---|---|---|---|---|
| F0A | 3.57 | 0 | 58.49 | 58.49 | <1 | nd | 1.41 | − |
| F0B | 7.14 | 0 | 57.44 | 57.44 | <1 | nd | 1.44 | − |
| F0C | 10.71 | 0 | 56.58 | 56.58 | <1 | nd | 1.47 | − |
| F0D | 14.29 | 0 | 55.84 | 55.84 | <1 | nd | 1.50 | − |
| F0E | 21.43 | 0 | 54.84 | 54.84 | <1 | nd | 1.53 | − |
| F0F | 28.57 | 0 | 53.75 | 53.75 | <1 | nd | 1.57 | − |
| F5A | 14.29 | 5 | 39.96 | 29.78 | 12.81 | 4.5 | 2.04 | − |
| F5B | 21.43 | 5 | 38.13 | 27.65 | 24.31 | 5.3 | 2.10 | − |
| F5C | 28.57 | 5 | 35.91 | 25.04 | 28.12 | 4.9 | 2.17 | − |
| F10A | 14.29 | 10 | 39.52 | 19.01 | 19.00 | 5.7 | 2.05 | − |
| F10B | 21.43 | 10 | 37.74 | 16.63 | 21.56 | 5.7 | 2.11 | − |
| F10C | 25.71 | 10 | 38.07 | 17.08 | 13.76 | nd | 2.10 | − |
| F12A | 18.57 | 12 | 38.51 | 13.50 | 28.48 | 6.2 | 2.08 | − |
| F15A | 14.29 | 15 | 38.32 | 6.95 | 21.37 | nd | 2.09 | − |
| F15B | 21.43 | 15 | 37.91 | 6.33 | 2.62 | 0.4 | 2.10 | − |
| F15C | 25.71 | 15 | 36.68 | 4.48 | <1 | 0.4 | 2.15 | + |
| F17A | 10.71 | 17.5 | 40.14 | 4.63 | <1 | 0.5 | 2.03 | + |
| F20A | 3.57 | 20 | 43.05 | 4.44 | <1 | nd | 1.93 | + | nd: not determined

In the different experiments the height, and thus the volume, of the press-moulded compacts was measured after having released the compaction pressure and after having carbonated the compacts. The total porosity of the compacts was calculated starting from this volume, the weight of the filler fraction (1500 grams) and the density of the filler particles (3392 kg/m$^3$). The unsaturated porosity was calculated as the total porosity minus the volume of water (1 kg of water being equal to 1 dm$^3$). The dry density obtained after press-moulding the compacts, i.e. before the carbonation step, was calculated starting from the volume of the compacts and the weight of the filler fraction. The amount of carbon dioxide taken up during the carbonation step was determined on the carbonated compacts by a DTA (Differential Thermal Analysis).

FIGS. 3A to 3D respectively show the unsaturated porosity, the compressive strength (after carbonation), the total porosity (before carbonation) and the dry density (before carbonation) of the compacts of the different experiments indicated in Table 1. By means of the computer program Surfer®9 lines of identical values were drawn in these figures.

Figure 3A:
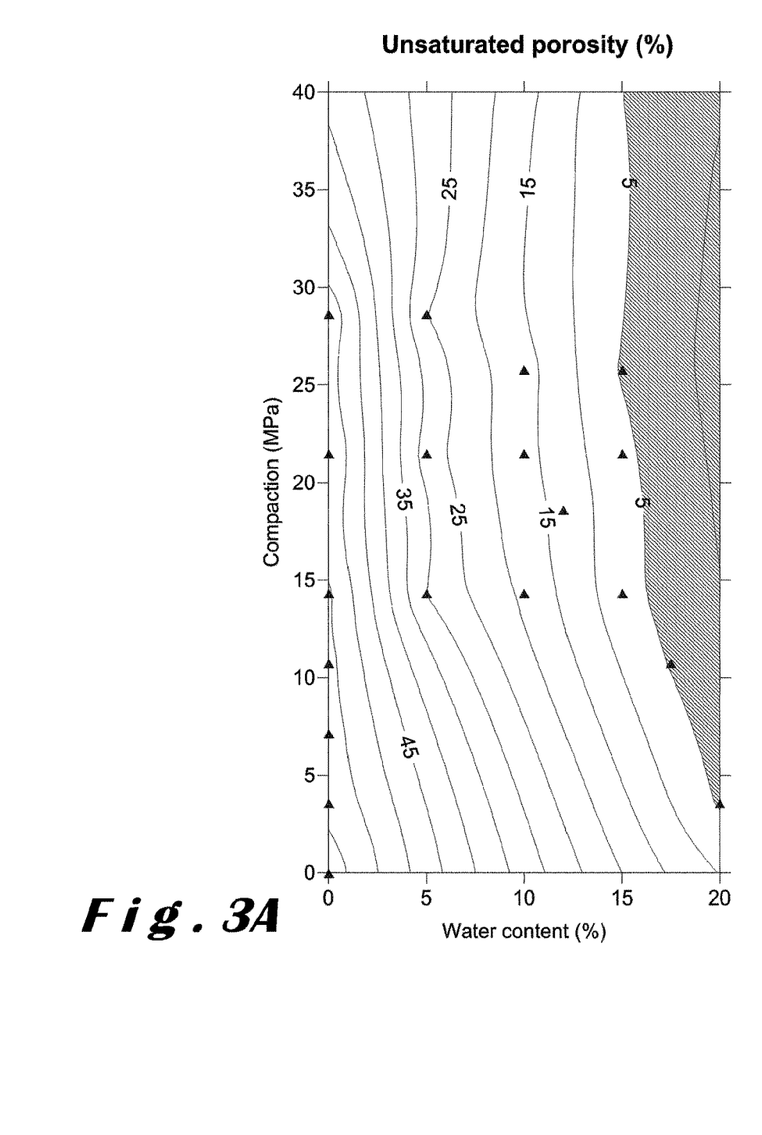
FIGS. 3A to 3D illustrate the test results obtained with the filler fraction in Experiment 1, FIG. 3A illustrating the calculated unsaturated porosity of the compacts, FIG. 3B the compressive strength of the carbonated compacts, FIG. 3C the calculated total porosity of the compacts and FIG. 3D the overall dry density of the compacts as a function of the water content of the compacts and the compaction pressure applied for press-moulding them.
Figure 3B:
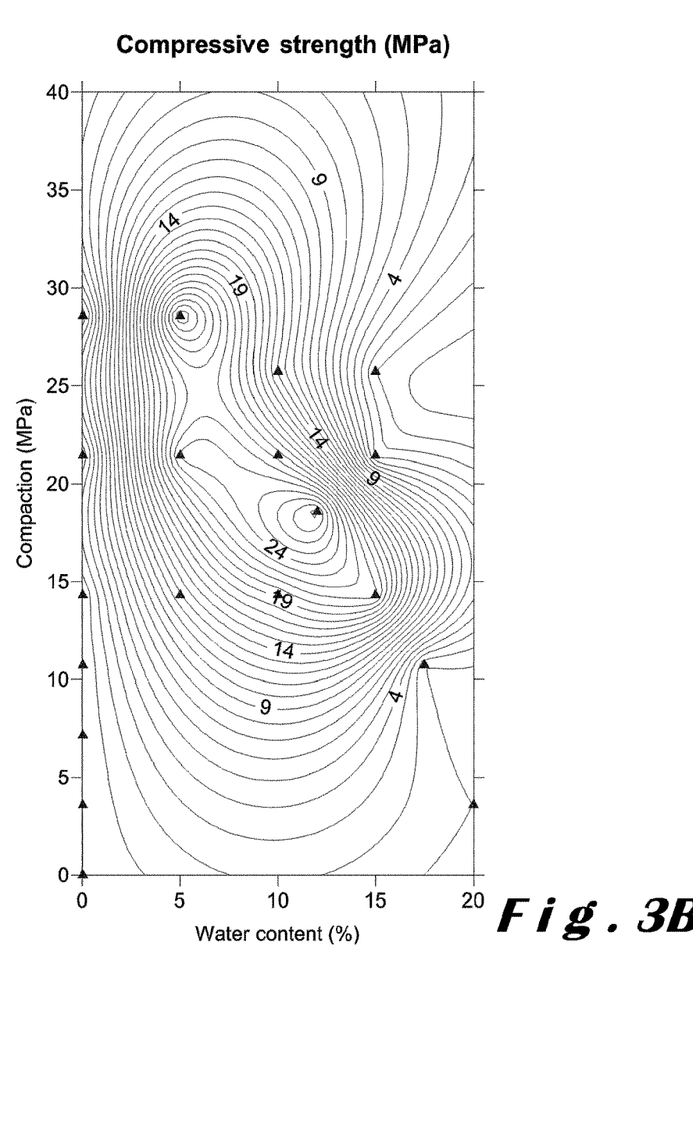
Figure 3C:
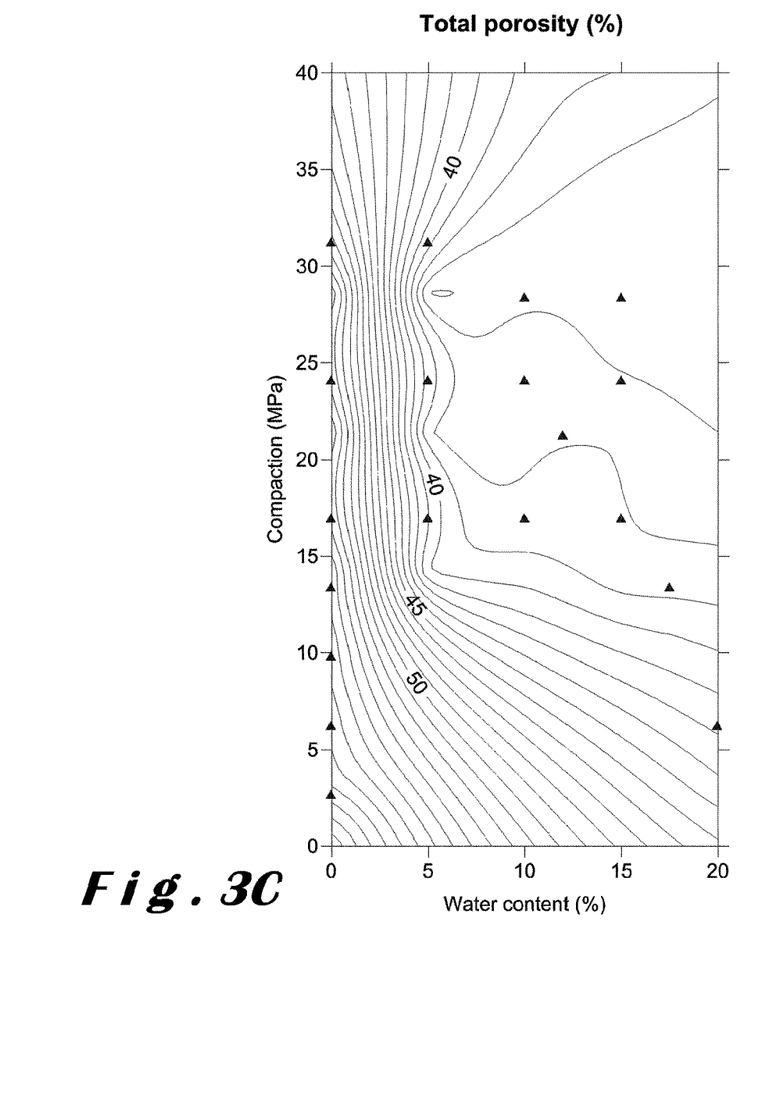
Figure 3D:
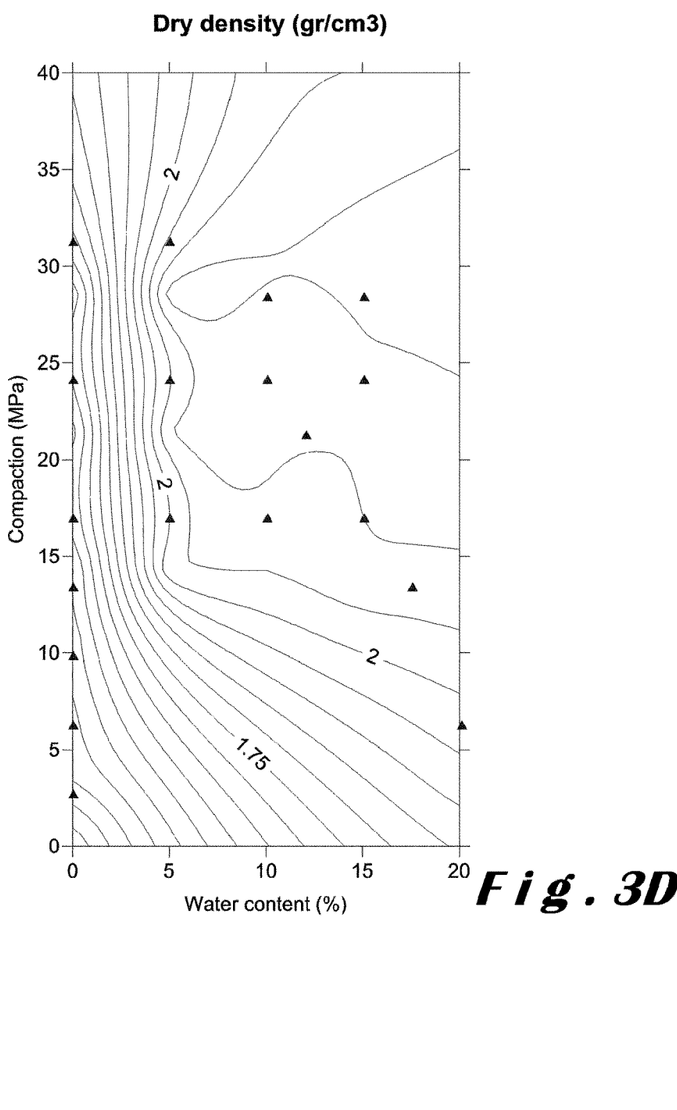

In FIGS. 3B to 3D, and in Table 1, it can be seen that as, for a same water content, the compaction pressure increases, and the dry density of the compacts increases (or the total porosity decreases), the compressive strength of the carbonated compacts increases. This is for example the case for the series of experiments F5A to F5C and for the series F10A to F10B. On the contrary, when the dry density of the compacts decreases (or the total porosity increases) upon an increase of the compaction pressure, the compressive strength of the carbonated compacts suddenly decreases. This is for example the case for the series of experiments F10B to F10C wherein the applied compaction pressure was respectively 21.4 and 25.7 MPa. For a water content of 10% by dry weight, the compaction pressure should thus be lower than 25.7 MPa so that, notwithstanding the lower compaction pressure, the compressive strength of the carbonated compacts increases from 13.8 MPa to 21.6 MPa.

In Experiments F15C, F17A and F20A the compaction pressure was increased until water started to be expelled from the compressed material, which occurred at the indicated compaction pressures. In FIGS. 3A to 3D it can be seen that when water starts to be expelled from the compacted material at these compaction pressures, the compaction pressure applied for press-moulding the compacts should be considerably lower than this compaction pressure. In Experiment F15C water started for example to be expelled at a compaction pressure of 25.7 MPa. Notwithstanding the fact that at this compaction pressure the dry density of the compact still increased (or the total porosity still decreased), the carbonated compact had nearly no strength (not measurable). A small decrease of the compaction pressure to 21.4 MPa in Experiment F15B resulted already a small compressive strength (of only 2.6 MPa) but a larger decrease of the compaction, to 14.3 MPa in Experiment F15A, resulted in a much larger compressive strength of 21.4 MPa. Consequently, even for relatively large water contents, the method of the present invention enables to achieve the most optimal compressive strengths without having to dry the material.

According to the invention, the compaction pressure applied for press-moulding the particulate material should be at least 7 MPa smaller than the compaction pressure at which water is expelled from the material. In Experiment F17A water was already expelled from the particulate material at a compaction pressure of 10.7 MPa, due to the relatively high water content of 17.5 wt. %. Lowering the compaction pressure to less than 3.7 MPa is however not possible in accordance with the present invention since the compaction pressure should be higher than 5 MPa. In case of a filler fraction that contains 17.5 wt. % or more of water, drying of the material, or mixing it with a drier particulate material is thus necessary.

From Experiments F15C, F17A and F20A, it appears that water is expelled from the press-moulded material when it is compressed with such a compaction pressure that the calculated unsaturated porosity is equal to about 4.5 vol. %. In reality the unsaturated porosity will be even somewhat larger since the particles of the filler fraction absorb a small amount of water, which is thus not present in the pores.

In FIG. 3B it can be seen that in particular for compaction pressures between 15 and 30 MPa, the compressive strength of the carbonated compacts strongly increases when increasing the water content of the compacts from 0 to 5% by dry weight. The total porosity also strongly decreases whilst the dry density correspondingly increases. For a water content of 0%, i.e. for a dry material, the compacts, even when press-moulded with a high compaction pressure, had only a minimal green strength (due to the too high porosity) so that they could not be handled by hand. The compacts with a higher water content, in particular a water content of 5% or higher, had on the contrary sufficient green strengths, which appears from the much lower total porosities of these compacts. For lower compaction pressures, in particular compaction pressures between 5 and 15 MPa, higher water contents enable to achieve lower porosities or higher dry densities resulting in higher compressive strengths. However, the obtained compressive strengths are generally lower than the compressive strengths obtained for lower water contents with higher compaction pressures.

Experiment 2

Fine Sand Fraction

Experiment 1 was repeated with the fine sand fraction of 0 to 0.5 mm of the stainless steel slag material. Other compaction pressures were however used and also an additional higher water content. The particle size distribution of the fine sand fraction is shown in FIG. 1.

The fine sand fraction strongly absorbed water. When storing it at 20° C. in an atmosphere which is saturated with water, it absorbs for example more than 15% of water. Proctor compaction tests carried out with such a fine sand fraction have shown that the highest packing density is achieved in the Proctor compaction test for a water content of about 22% by dry weight. The packing density obtained in the Proctor compaction test corresponds to the packing density obtained with a relatively low compaction pressure, in particular a compaction pressure of between 10 and 15 MPa.

The applied parameters and the measured and calculated test results are indicated in Table 2.

TABLE 2

Experiments with the carbonation of the 0 to 0.5 mm fine sand fraction of stainless steel slag press-moulded with different compaction pressures and having different water contents.

| Exp. | Comp. pressure (MPa) | Water (wt. %) | Total porosity (vol. %) | Unsat. porosity (vol. %) | Compr. strength (MPa) | Dry density (g/cm$^3$) | Water expelled |
|---|---|---|---|---|---|---|---|
| S0A | 7.75 | 0 | 44.49 | 44.49 | | 1.67 | – |
| S0B | 15.42 | 0 | 43.30 | 43.30 | | 1.71 | – |
| S0C | 23.11 | 0 | 41.47 | 41.47 | | 1.76 | – |
| S0D | 30.62 | 0 | 40.35 | 40.35 | | 1.80 | – |
| S0E | 38.30 | 0 | 39.47 | 39.47 | | 1.82 | – |
| S5A | 7.72 | 5 | 44.23 | 35.84 | 10.01 | 1.68 | – |
| S5B | 15.44 | 5 | 41.53 | 32.73 | 15.72 | 1.76 | – |
| S5C | 23.10 | 5 | 40.39 | 31.42 | 18.00 | 1.79 | – |
| S5D | 30.72 | 5 | 38.64 | 29.40 | 24.87 | 1.85 | – |
| S5E | 38.39 | 5 | 36.88 | 27.38 | 31.16 | 1.90 | – |
| S10A | 7.70 | 10 | 44.64 | 27.98 | 16.89 | 1.67 | – |
| S10B | 15.38 | 10 | 41.55 | 23.95 | 27.90 | 1.76 | – |
| S10C | 23.08 | 10 | 39.39 | 21.15 | 29.25 | 1.82 | – |
| S10D | 30.61 | 10 | 37.81 | 19.09 | 33.68 | 1.87 | – |
| S10F | 38.39 | 10 | 36.84 | 17.83 | 40.78 | 1.90 | – |
| S15A | 7.70 | 15 | 45.06 | 20.26 | 18.59 | 1.65 | – |
| S15B | 15.39 | 15 | 40.72 | 13.96 | 25.43 | 1.78 | – |
| S15C | 23.04 | 15 | 39.07 | 11.56 | 23.95 | 1.83 | – |
| S15C | 30.64 | 15 | 37.66 | 9.51 | 15.32 | 1.88 | – |
| S15E | 38.28 | 15 | 33.27 | 3.91 | 7.05 | 2.01 | – |
| S20A | 7.67 | 20 | 43.32 | 9.19 | 7.40 | 1.71 | – |
| S20B | 15.30 | 20 | 41.21 | 5.82 | 5.83 | 1.77 | – |

TABLE 2-continued

Experiments with the carbonation of the 0 to 0.5 mm fine sand fraction of stainless steel slag press-moulded with different compaction pressures and having different water contents.

| Exp. | Comp. pressure (MPa) | Water (wt. %) | Total porosity (vol. %) | Unsat. porosity (vol. %) | Compr. strength (MPa) | Dry density (g/cm³) | Water expelled |
|---|---|---|---|---|---|---|---|
| S20C | 23.89 | | | | | | |
| S25A | 7.66 | 25 | 43.40 | 0.81 | | 1.70 | + |

In the different experiments the height, and thus the volume, of the press-moulded compacts was measured after having released the compaction pressure and after having carbonated the compacts. The total porosity of the compacts was calculated starting from this volume, the weight of the fine sand fraction (1500 grams) and the density of the slag sand particles (3000 kg/m³). The unsaturated porosity was calculated as the total porosity minus the volume of water (1 kg of water being equal to 1 dm³). The dry density obtained after press-moulding the compacts, i.e. before the carbonation step, was calculated starting from the volume of the compacts and the weight of the fine sand fraction.

FIGS. 4A to 4D respectively show the unsaturated porosity, the compressive strength (after carbonation), the total porosity (before carbonation) and the dry density (before carbonation) of the compacts of the different experiments indicated in Table 2.

Figure 4A:
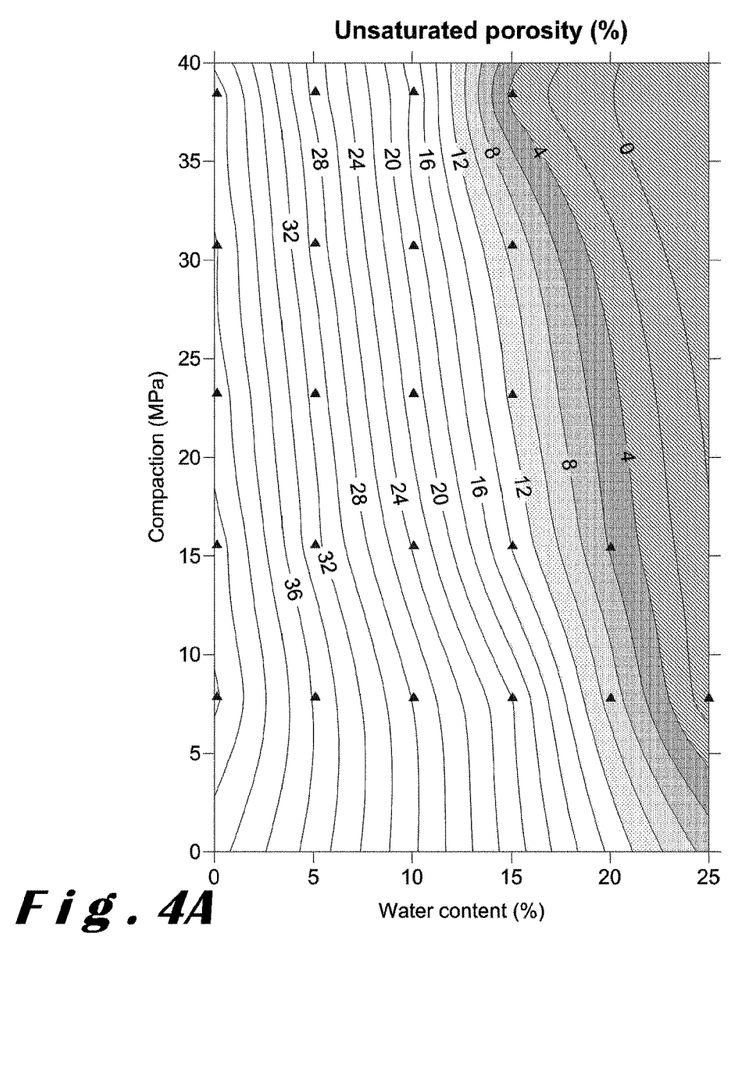
FIGS. 4A to 4D are the same as FIGS. 3A to 3D but illustrate the results obtained with the fine sand fraction in Experiment 2.
Figure 4B:
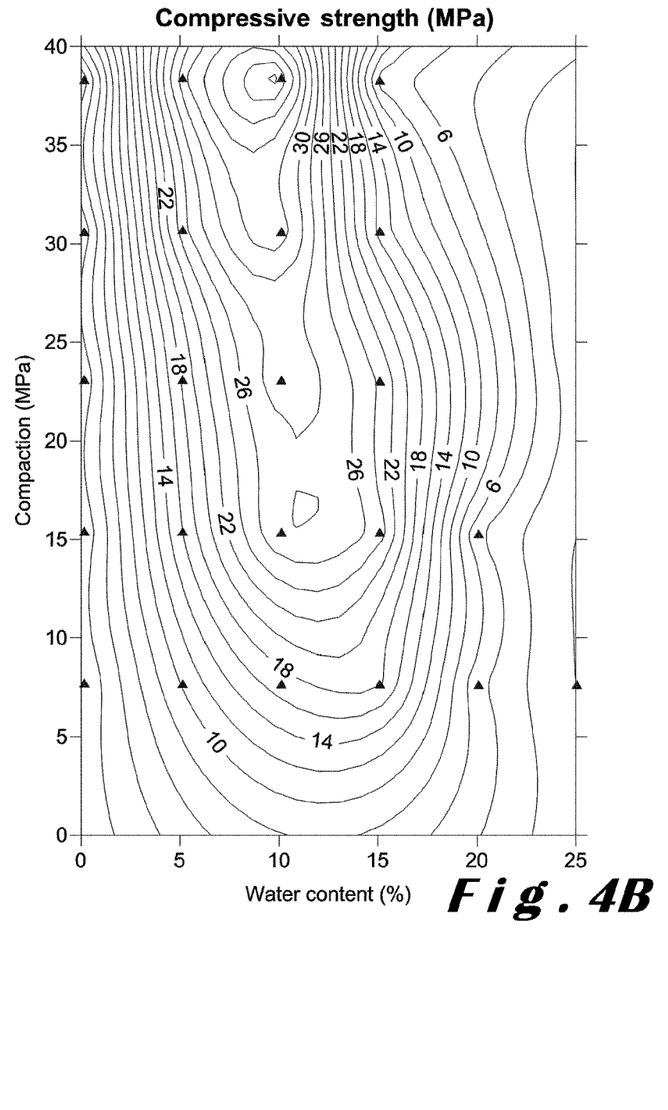
Figure 4C:
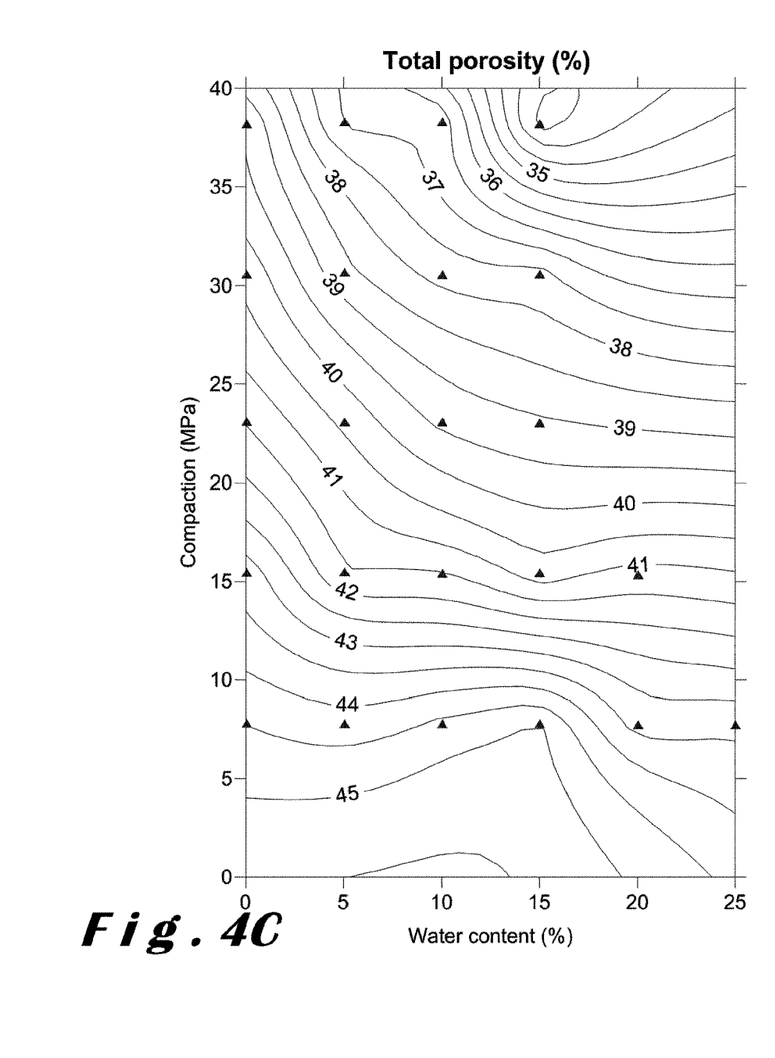
Figure 4D:
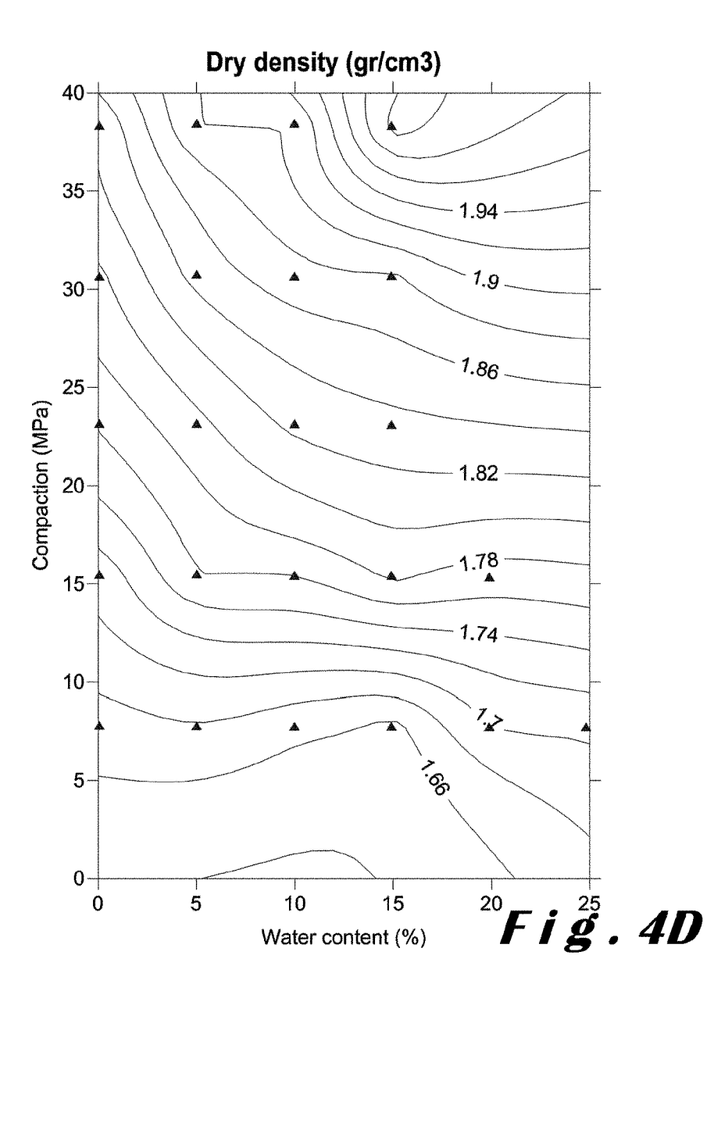

In FIGS. 4B to 4D, and in Table 2, it can be seen that as, for a same water content, the compaction pressure increases, and the dry density of the compacts increases (or the total porosity decreases), the compressive strength of the carbonated compacts increases. This is for example the case for the series of experiments S5A to S5E and S10A to S10F. In contrast to the filler fraction, a decrease of the dry density of the compacts upon an increase of the compaction pressure has not been observed in the experiments carried out with the fine sand fraction. This may be due to a different structure or composition of the fine sand particles or maybe due to a more equilibrated particle size distribution thereof. The method of the present invention does not require examination of the structure or particle size distribution of the particles but simply requires testing of the effect of an increase of the compaction pressure upon the dry density of the compacts.

In FIGS. 4A to 4D it can also be seen that when water starts to be expelled from the compacted material at a certain compaction pressure, the compaction pressure applied for press-moulding the compacts should be considerably lower than this compaction pressure. In Experiment S25A the fine sand fraction was compressed to achieve an unsaturated porosity of only 0.8% so that a considerable amount of water was expelled from the compressed material. As a matter of fact, another experiment has shown that water starts to be expelled from the fine sand fraction as soon as its calculated unsaturated porosity (not taking into account the water absorbed by the sand particles themselves) is reduced to 3 vol. %. The fact that this unsaturated porosity is smaller than the unsaturated porosity of the filler fraction may be explained by the fact that the particles of the fine sand fraction absorb more water than the particles of the filler fraction.

For a water content of 15% by dry weight, the compressive strength increased when increasing the compaction pressure from 7.7 to 15.4 MPa (Exp. S15A to S15B) but then decrease when the compaction pressure is further increased from 15.4 to 38.3 MPa (Exp. S15B to S15E), notwithstanding the fact that the porosity decreased. Since the porosity was reduced in Experiment S15E to only 3.14 vol. %, it is clear that with a somewhat larger compaction pressure, water would start to be expelled from the material. In order to achieve a sufficiently high compaction pressure, in particular a compaction pressure of at least 10 MPa (which is for example an essential element of the definition of "shape retaining mass" in the Belgian legislation), a lower compaction pressure should thus be used for such a high water content. For lower water contents, in particular for a water content of 5% by dry weight, higher compaction pressures result in higher compressive strengths. However, since drying of the wet fine sand fraction is to be avoided, in case the fine sand fraction has a water content of 15% by dry weight, the method of the present invention allows to obtain quite high compressive strength of about 25 MPa by simple using a lower compaction pressure of 15 MPa for such a relatively high water content. On the other hand, if the water content is still higher, for example 20% by weight, such high compressive strengths cannot be achieved. A drying step can however be avoided by mixing for example 75 wt. % of the fine sand fraction (containing 20% of water) with 25 wt. % of the filler fraction (containing less than 0.3% of water) to obtain a mixture containing about 15% of water.

In FIG. 4B it can be seen that in particular for compaction pressures between 15 and 30 MPa, the compressive strength of the carbonated compacts strongly increases when increasing the water content of the compacts from 0 to 5% by dry weight. Compared to the filler fraction, the total porosity did however decrease less strongly. A similar increase of the compressive strength can however possibly be explained by the fact that the particles of the fine sand fraction absorb more water than the filler fraction so that the addition of more water does not only reduces the porosity but may also enhance the carbonation reaction.

The invention claimed is:

1. A method for producing carbonate bonded, press-moulded articles, which method comprises the steps of:
    providing a particulate material which is carbonatable and which contains water;
    press-moulding the particulate material to form compacts; and
    carbonating the particulate material in said compacts to produce carbonates thus transforming the compact into said carbonate bonded, press-moulded articles, the particulate material being carbonated by bringing the compacts in contact with a gas which contains at least 1 vol. % of carbon dioxide,
    wherein
    before press-moulding the particulate material to form said compacts, at least one sample thereof is subjected to a test wherein the sample is compressed with an increasing compaction pressure until water starts to be expelled from said sample as from a lower compaction pressure; and
    the particulate material is press-moulded to form said compacts with a compaction pressure which is selected within a range delimited by a lower and an upper compaction pressure limit, the lower compaction pressure limit being higher than 5 MPa and the upper compaction pressure limit being at least 7 MPa smaller than said lower compaction pressure.

2. The method as claimed in claim 1, wherein said upper compaction pressure limit is at least 10 MPa smaller than said lower compaction pressure.

3. The method as claimed in claim 1, wherein said upper compaction pressure limit is smaller than 60 MPa.

4. The method as claimed in claim 1, wherein said lower compaction pressure limit is larger than 7 MPa.

5. The method as claimed in claim 1, wherein the particulate material comprises slag from a metal production process, slag from the production of phosphorus, bottom ash and/or fly ash.

6. The method as claimed in claim 1, wherein said particulate material is prepared by mixing a first particulate material, which is carbonatable, with a second particulate material, which is not carbonatable.

7. The method as claimed in claim 6, wherein said second particulate material comprises dust extracted from flue gasses from a steel converter and/or waste resulting from deburring of steel parts.

8. The method as claimed in claim 1, comprising the step of increasing the water content of the particulate material which is provided to be press-moulded and carbonated to a predetermined water content thereby increasing the compressive strength of said compacts before being carbonated.

9. The method as claimed in claim 8, wherein the water content of said particulate material is increased to said predetermined water content by adding water to said particulate material and/or by composing said particulate material as a mixture of an amount of a first particulate material, having a first water content, and an amount of a second particulate material, having a second water content which is lower than said first water content, and by increasing the ratio between the amount of said first particulate material to the amount of said second particulate material.

10. The method as claimed in claim 1, comprising the step of decreasing the water content of the particulate material which is provided to be press-moulded and carbonated to a predetermined water content, which is higher than 3% by dry weight.

11. The method as claimed in claim 10, wherein the water content of said particulate material is decreased to said predetermined water content by drying the particulate material and/or by composing said particulate material as a mixture of an amount of a first particulate material, having a first water content, with an amount of a second particulate material, having a second water content which is lower than said first water content, and by decreasing the ratio between the amount of said first particulate material to the amount of said second particulate material.

12. The method as claimed in claim 11, wherein said first particulate material comprises a stainless steel slag material which contains at least 3% by dry weight of γ-dicalcium silicate.

13. The method as claimed in claim 12, wherein said second particulate material comprises a stainless steel slag material which contains less γ-dicalcium silicate than said first particulate material.

14. The method as claimed in claim 1, wherein said gas contains at least 3 vol. %, preferably at least 5 vol. % and more preferably at least 7 vol. % of carbon dioxide.

15. The method as claimed in claim 1, wherein said gas is at a gauge pressure of less than 0.5 MPa.

16. The method as claimed in claim 1, wherein the particulate material which is press-moulded to form said compacts has a water content of at least 1% by dry weight.

17. The method as claimed in claim 1, wherein at least 50 vol. % of said particulate material has a particle size smaller than 1000 μm and at least 50 vol. % of said particulate material has a particle size larger than 1 μm.

\* \* \* \* \*